United States Patent
Nakano et al.

(10) Patent No.: US 12,133,661 B2
(45) Date of Patent: Nov. 5, 2024

(54) MEDICAL DEVICE

(71) Applicant: TERUMO KABUSHIKI KAISHA, Tokyo (JP)

(72) Inventors: Taiga Nakano, Cupertino, CA (US); Junichi Kobayashi, Cupertino, CA (US); Tomonori Hatta, San Jose, CA (US); Kosuke Nishio, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1027 days.

(21) Appl. No.: 17/014,083

(22) Filed: Sep. 8, 2020

(65) Prior Publication Data
US 2020/0397466 A1  Dec. 24, 2020

Related U.S. Application Data

(63) Continuation of application No. PCT/JP2019/011690, filed on Mar. 20, 2019.

(30) Foreign Application Priority Data

Mar. 28, 2018 (JP) ................. 2018-062328

(51) Int. Cl.
*A61B 17/3207* (2006.01)
*A61B 17/22* (2006.01)

(52) U.S. Cl.
CPC ........... *A61B 17/320758* (2013.01); *A61B 2017/22079* (2013.01); *A61B 2017/22082* (2013.01)

(58) Field of Classification Search
CPC .. A61B 17/320758; A61B 2017/22079; A61B 2017/22082; A61B 2217/005; A61B 2217/007
See application file for complete search history.

(56) References Cited

U.S. PATENT DOCUMENTS

| | | |
|---|---|---|
| 4,591,355 A | 5/1986 | Hilse |
| 5,501,694 A | 3/1996 | Ressemann et al. |
| | (Continued) | |

FOREIGN PATENT DOCUMENTS

| | | |
|---|---|---|
| JP | S6120562 A | 1/1986 |
| JP | H08509639 A | 10/1996 |
| | (Continued) | |

OTHER PUBLICATIONS

International Search Report (with English Translation) and Written Opinion issued in corresponding International Patent Application No. PCT/JP2019/011690, 11 pages (May 21, 2019).

(Continued)

*Primary Examiner* — Brooke Labranche
(74) *Attorney, Agent, or Firm* — BUCHANAN INGERSOLL & ROONEY PC (57) ABSTRACT

A medical device is able to achieve a high aspiration pressure while also effectively transmitting rotational torque to a cutting portion to remove an object inside a biological lumen. The medical device includes a drive shaft, an outer tube accommodating the drive shaft, a cutting portion fixed to the drive shaft, and a hub unit. The hub unit has a first housing with an aspiration port, a second housing with a liquid delivering port, and first and second seal portions disposed between the second housing and the drive shaft. The first seal portion has a first frictional coefficient, and the second seal portion has a second frictional coefficient. The first frictional coefficient is lower than the second frictional coefficient, and the first seal portion is located on a distal side of the second seal portion.

20 Claims, 5 Drawing Sheets

(56) References Cited

U.S. PATENT DOCUMENTS

| | | | |
|---|---|---|---|
| 8,475,484 B2 | 7/2013 | Wulfman et al. | |
| 2015/0335348 A1 | 11/2015 | Cohen et al. | |
| 2017/0354435 A1* | 12/2017 | Hatta | A61B 17/320725 |
| 2019/0290314 A1* | 9/2019 | Gemer | A61M 29/00 |

FOREIGN PATENT DOCUMENTS

| | | |
|---|---|---|
| JP | 2016501696 A | 1/2016 |
| WO | 2016072107 A1 | 5/2016 |

OTHER PUBLICATIONS

An English Translation of the International Search Report (Form PCT/ISA/210) and the Written Opinion of the International Searching Authority (Form PCT/ISA/237) issued on May 21, 2019, by the Japanese Patent Office in corresponding International Application No. PCT/JP2019/011690. (10 pages).

* cited by examiner

MEDICAL DEVICE

CROSS-REFERENCES TO RELATED APPLICATIONS

This application is a continuation of International Application No. PCT/JP2019/011690 filed on Mar. 20, 2019, which claims priority to Japanese Application No. 2018-062328 filed on Mar. 28, 2018, the entire content of both of which is incorporated herein by reference.

FIELD OF THE INVENTION

The present invention generally relates to a medical device and method for removing an object in a biological lumen.

BACKGROUND DISCUSSION

Examples of methods for treating a stenosed site caused by plaque or a thrombus in a blood vessel include a method of widening the blood vessel with a balloon and a method of causing a mesh-shaped or coil-shaped stent to indwell the blood vessel as a support for the blood vessel. However, according to the methods, it is difficult to treat the stenosed site hardened by calcification or the stenosed site appearing in a bifurcated portion of the blood vessel. As a method which enables treatment even in this case, a method of cutting and removing a stenosed object such as the plaque and the thrombus is known.

For example, in U.S. Pat. No. 8,475,484, a device is disclosed in which an operation head for cutting an object is fixed to a distal portion of a drive shaft. The device rotates the drive shaft, thereby enabling the operation head to cut the object. An operator's hand side of the device has a sealing structure for internally sealing the device. The sealing structure includes an injection port for injecting a sealing fluid and an aspiration port for aspirating the fluid. A seal portion through which the drive shaft penetrates is disposed on a proximal side of the injection port.

SUMMARY

The device disclosed in U.S. Pat. No. 8,475,484 has a constant clearance between the drive shaft and the seal portion. When the clearance increases, frictional resistance of the seal portion is reduced, and torque transmission efficiency is improved. However, sealing performance of the seal portion is degraded. When the clearance decreases, the sealing performance of the seal portion is improved. However, the frictional resistance of the seal portion increases. Accordingly, the torque transmission efficiency of the drive shaft is degraded.

The medical device disclosed here can achieve a high aspiration pressure and can effectively transmit a rotational torque to a cutting portion.

The medical device for removing an object inside a biological lumen includes a rotatable drive shaft, an outer tube that accommodates the drive shaft to be rotatable, a cutting portion fixed to a distal portion of the drive shaft to cut the object, and a hub unit disposed in a proximal portion of the drive shaft and the outer tube. The hub unit has a first housing having an aspiration port for discharging a fluid to an outside, and causing a lumen of the outer tube to communicate with the aspiration port, a second housing having a liquid delivering port for delivering a liquid from the outside, and causing a lumen of the drive shaft to communicate with the liquid delivering port, a first seal portion disposed between the second housing and the drive shaft, and having a first frictional coefficient, and a second seal portion disposed between the second housing and the drive shaft, and having a second frictional coefficient. The first frictional coefficient is lower than the second frictional coefficient, and the first seal portion is located on a distal side of the second seal portion.

According to the medical device configured as described above, the first seal portion having the lower frictional coefficient is disposed on a high pressure side of the second seal portion having the higher frictional coefficient. In this manner, the first seal portion and the second seal portion are combined with each other. Accordingly, the frictional coefficient can be reduced while sealing performance can be sufficiently achieved. Therefore, the medical device can effectively transmit a rotational torque to the cutting portion while a high aspiration pressure can be achieved.

According to another aspect, a medical device for removing an object inside a biological lumen comprises an outer tube, a rotatable drive shaft, a cutter and a housing. The outer tube includes a lumen having an open distal end that opens to outside the outer tube at a distal end portion of the outer tube. The rotatable drive shaft is accommodated in the lumen of the outer tube so that the drive shaft accommodated in the lumen of the outer tube is rotatable relative to the outer tube. The drive shaft includes a lumen possessing an open distal end that opens to outside the drive shaft at a distal end portion of the drive shaft, with a space between an outer surface of the drive shaft and an inner surface of the outer tube. The cutter is fixed to the distal end portion of the drive shaft and is rotatable together with the rotatable drive shaft to cut the object. A space is located in the housing, and the housing includes a liquid delivering port that communicates with the space in the housing so the liquid flowing through the liquid delivering port flows into the space in the housing, with the lumen of the drive shaft being in communication with the space in the housing so that liquid entering the space in the housing by way of the liquid delivering port enters the lumen in the drive shaft and at least some of the liquid entering the lumen in the drive shaft flows along the lumen in the drive shaft and flows out through the open distal end of the lumen in the drive shaft. The drive shaft passes through the space in the housing, and a first seal surrounds the drive shaft and possesses an inner surface and an outer surface. The first seal is positioned between the housing and the drive shaft so that the outer surface of the first seal faces the housing and the inner surface of the first seal faces the drive shaft. The inner surface of the first seal possesses a first frictional coefficient. A second seal surrounds the drive shaft and possesses an inner surface and an outer surface. The second seal is positioned between the housing and the drive shaft so that the outer surface of the second seal faces the housing and the inner surface of the second seal faces the drive shaft. The inner surface of the second seal possesses a second frictional coefficient. The second seal is positioned proximal of the first seal, and the first frictional coefficient is different from the second frictional coefficient.

In accordance with another aspect, a method comprises inserting a cutter into a biological lumen and advancing the cutter in the biological lumen to position the cutter adjacent an object in the lumen that is to be removed. The cutter is connected to a distal portion of a rotatable drive shaft so that the cutter rotates together with the drive shaft, and the drive shaft includes a lumen and is accommodated in a lumen in an outer tube so that the outer tube surrounds the drive shaft.

The lumen in the drive shaft communicates with a space in a housing, and the drive shaft passes through the housing with a portion of the drive shaft located in the housing. The method also comprises rotatably driving the drive shaft to rotate the cutter while the cutter is in contact with the object to cut the object, and introducing liquid into the space in the housing so that the liquid enters the lumen in the drive shaft and at least some of the liquid in the lumen in the drive shaft flows in a distal direction and flows out of the lumen in the drive shaft by way of an open end of the lumen. The open end of the lumen in the drive shaft is at the distal portion of the drive shaft. The method further comprises sealing the drive shaft and the housing by way of two seals positioned proximal of the space in the housing to prevent the liquid introduced into the space of the housing from flowing out between the drive shaft and the second housing, wherein the first and second seals are positioned between the housing and the drive shaft with the first seal on a distal side of the second seal, and wherein the first seal possesses a first frictional coefficient and the second seal possessing a second frictional coefficient different from the first frictional coefficient.

BRIEF DESCRIPTION OF THE DRAWINGS

FIGS. 4A to 4C are views illustrating a state where a lesion area is removed by the medical device according to a first embodiment.

FIGS. 5A to 5C are cross-sectional views illustrating modification examples of the medical device.

FIGS. 6A and 6B are cross-sectional views illustrating modification examples of the medical device.

DETAILED DESCRIPTION

Set forth below with reference to the accompanying drawings is a detailed description of embodiments of a medical device and method for removing an object in a biological lumen, representing examples of the inventive medical device and method disclosed here. In some cases, a size or a ratio of each member in the drawings may be exaggerated for convenience of description, and may be different from an actual size or an actual ratio.

A medical device 10 according to an embodiment is inserted into a blood vessel in an acute lower limb ischemia or a deep vein thrombosis, and is used for a treatment to destroy and remove a thrombus, plaque, an atheroma, a calcified lesion or the like. In the present specification, a side of the device which is inserted into the blood vessel is referred to as a "distal side", and an operator's hand side is referred to as a "proximal side". Though the medical device described here has useful application to destroy the thrombus, the plaque, the atheroma, or the calcified lesion, the medical device disclosed here is not limited in this regard and is applicable to any object that may be present inside a biological lumen.

Figure 1:
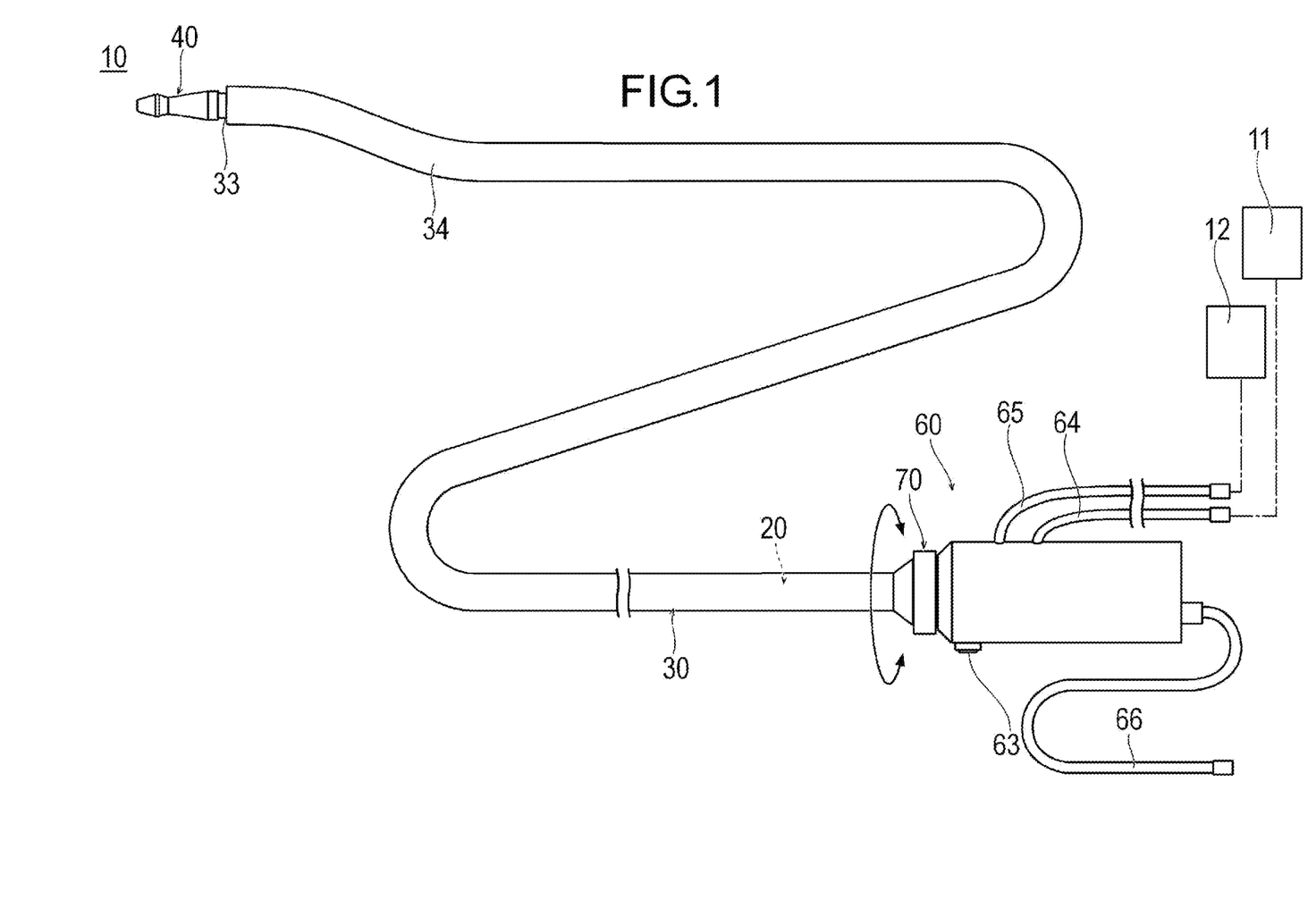
FIG. 1 is a plan view illustrating a medical device according to an embodiment.
Figure 2:
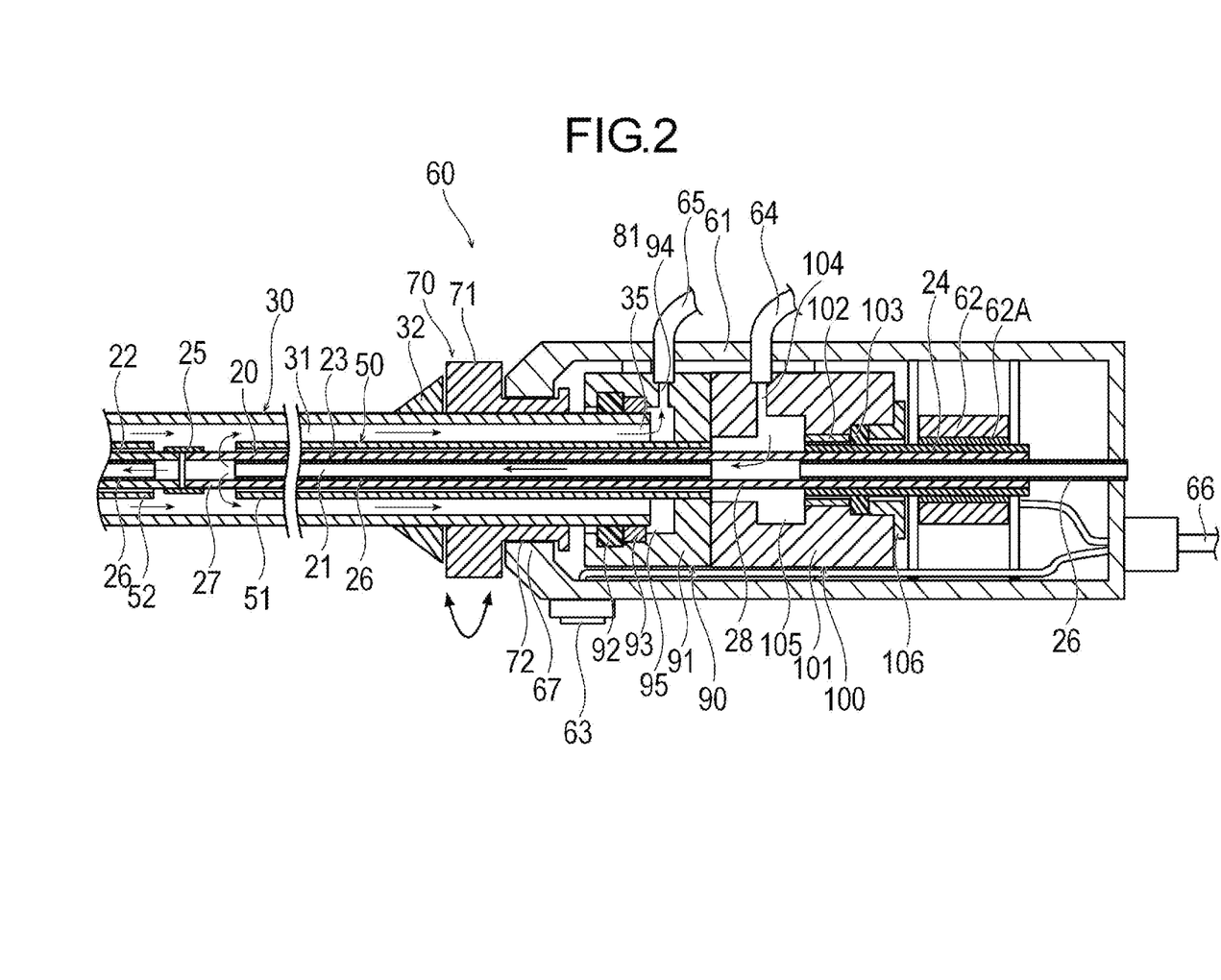
FIG. 2 is a sectional view illustrating a proximal portion of the medical device.
Figure 3:
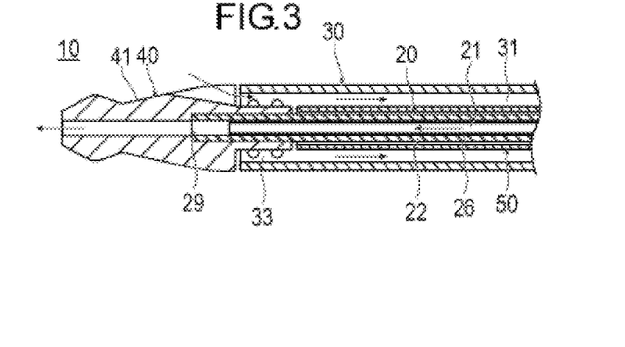
FIG. 3 is a sectional view illustrating a distal portion of the medical device.

As illustrated in FIGS. 1 to 3, the medical device 10 includes an elongated drive shaft 20 that is rotationally driven, an inner tube 50 that accommodates the drive shaft, an outer tube 30 that accommodates the drive shaft 20 and the inner tube 50, a cutting portion (cutter) 40 that cuts the thrombus, and a hub unit 60.

The drive shaft 20 is elongated, and transmits a rotational force to the cutting portion 40. The drive shaft 20 has a liquid delivering lumen 21 for delivering a liquid such as physiological salt solution to the distal side. The liquid delivering lumen 21 also serves as a guide wire lumen through which a guide wire passes. The drive shaft 20 includes a first drive shaft 22, a second drive shaft 23 located on the proximal side of the first drive shaft 22, and a drive tube 24 fixed to a proximal portion of the second drive shaft 23. The drive shaft 20 further includes a tubular interlock portion 25 that interlocks the first drive shaft 22 and the second drive shaft 23 with each other, and a protective tube 26.

The first drive shaft 22 and the second drive shaft 23 are flexible, and have a characteristic in which rotational power acting from the proximal side can be transmitted to the distal side. The first drive shaft 22 and the second drive shaft 23 are tubular bodies in which a plurality of wire rods (wires) are arrayed and interlocked with each other in a spiral shape. That is, each of the drive shafts 22, 23 is formed by at least one spirally wound wire. Therefore, the first drive shaft 22 and the second drive shaft 23 allow a fluid to pass through a gap (gaps) between the wire rods. Spiral winding directions of the first drive shaft 22 and the second drive shaft 23 are opposite to each other. The cutting portion 40 is fixed to a distal portion of the first drive shaft 22.

The drive tube 24 is fixed to a proximal portion of the second drive shaft 23. The drive tube 24 is a rigid tubular body that receives a rotational torque from a drive unit 62 (to be described later). The drive tube 24 penetrates the drive unit 62, and rotates inside the drive unit 62 via a rotating drive rotor 62A of the drive unit 62 and a bearing (not illustrated). A material from which the drive tube 24 may be fabricated preferably has a certain degree of rigidity so that the torque can be effectively transmitted, and for example, metal materials can be preferably used. Through laser processing, a spiral slit or groove can be formed on an outer periphery of the metal materials. In this manner, torque transmission performance can be improved. In addition to the metal materials, in order to improve electrical safety, the drive tube 24 can be formed of non-conductive metal or an insulating material such as a resin. For example, the material from which the drive tube 24 may be made may include metal materials such as stainless steel, Ta, Ti, Pt, Au, W, polyolefin such as polyethylene and polypropylene, polyamide, polyester such as polyethylene terephthalate, polytetrafluoroethylene (PTFE), fluorine-based polymer such as ethylene-tetrafluoroethylene copolymer (ETFE), polyether ether ketone (PEEK), polyimide, polyacetal (POM), natural rubber, synthetic rubber, silicone resin, and further a combination of two or more of the materials (polymer alloy, polymer blend, laminate, coating, partial arrangement or the like). In addition, in order to maintain rigidity, the drive tube 24 may have the above-described resin material disposed on the outer periphery of the above-described metal material.

The protective tube 26 is a tubular body that covers the insides of the first drive shaft 22, the second drive shaft 23, and the drive tube 24. The protective tube 26 prevents a guide wire passing through the liquid delivering lumen 21 from rubbing against the first drive shaft 22, the second drive shaft 23, and the drive tube 24. The protective tube 26 is partially disconnected in order to allow a fluid to pass therethrough inside an interlock portion between the first drive shaft 22 and the second drive shaft 23, and a second space portion 105 (to be described later). That is, as shown in FIG. 2, the protective tube 26 may be comprised of segments so that a portion of the protective tube 26 does not exist in the interlock portion between the first drive shaft 22 and the second drive shaft 23, and so that a portion of the protective tube 26 does not exist in the second space portion 105. The protective tube 26 may be continuous in the interlock portion between the first drive shaft 22 and the second drive shaft 23 so that the protective tube 26 spans across the interlock portion between the first drive shaft 22 and the second drive shaft 23. Furthermore, instead of being partially disconnected, a side hole communicating with an outer surface from an inner surface of the protective tube 26 may be provided. A proximal end of the protective tube 26 extends to a proximal end of the hub unit 60 to prevent the guide wire from rubbing inside the hub unit 60 and to guide the guide wire.

The vicinity of the interlock portion between the first drive shaft 22 and the second drive shaft 23 of the drive shaft 20 is a central passage portion 27 through which the fluid existing inside (liquid delivering lumen 21) passes outward. A portion located inside the second space portion 105 of the drive shaft 20 is a proximal passage portion 28 through which the liquid in the second space portion 105 passes inward (liquid delivering lumen 21). A distal end of the drive shaft 20 has a discharge opening portion 29 for discharging the liquid.

Examples of the material for fabricating the first drive shaft 22 and the second drive shaft 23 may preferably include stainless steel, Ta, Ti, Pt, Au, W, polyolefin such as polyethylene and polypropylene, polyamide, polyester such as polyethylene terephthalate, and fluorine-based polymer such as ETFE, polyether ether ketone (PEEK), and polyimide. The drive shaft 20 may not be divided into two parts, namely the first drive shaft 22 and the second drive shaft 23. The drive shaft may not be formed of a spiral wire rod. For example, the drive shaft may have a spiral slit or groove formed through laser processing.

The outer tube 30 is a cylindrical body that accommodates the drive shaft 20 and the inner tube 50. The outer tube 30 has an aspiration lumen 31 for aspirating an object such as a cut thrombus. An anti-kink protector 32 and an operation unit 70 are fixed to an outer peripheral surface of the proximal portion of the outer tube 30. The anti-kink protector 32 prevents kinks on the proximal side of the outer tube 30. In the outer tube 30, an aspiration seal portion 92 and a second support portion 93 (to be described later) are in contact with an outer surface on the proximal side from a portion interlocked with the operation unit 70. A portion with which the operation unit 70 of the outer tube 30 is interlocked and a portion on the further proximal side are rigid. Similarly, at least some of the portion of the operation unit 70 which is interlocked with the outer tube 30 is rigid. Therefore, the outer tube 30 can be in satisfactorily contact with the operation unit 70, the aspiration seal portion (aspiration seal) 92, and the second support portion (second support) 93. The outer surface of the operation unit 70, which comes into contact with the aspiration seal portion 92 and the second support portion 93, is smoothly formed to allow low friction contact. The operation unit 70 preferably has a certain degree of strength. As a material for fabricating the operation unit 70, it is possible to preferably use ABS resin, or resin such as polycarbonate (PC), polymethyl methacrylate (PMMA), polyacetal (POM), polyphenylsulfone (PPSU), polyethylene (PE), carbon fiber, and polyether ether ketone (PEEK). A rotary operation may be stabilized by using metal such as stainless steel, Ta, Ti, Pt, Au, and W, that is, a high density material. The outer surface of the operation unit 70 which an operator touches may form a high friction surface. In this manner, a reliable and accurate rotational torque operation can be realized by the operator. The high friction surface may be formed of a biocompatible high friction material such as butyl rubber, isoprene rubber, butadiene rubber, silicone rubber, natural rubber, polyvinyl chloride (PVC), polypropylene (PP), polyethylene (PE). Alternatively, the outer surface may have irregularities so that the outer surface is easily caught by the operator's finger. The outer surface of the proximal portion of the outer tube 30 has a high frictional force except for a portion in contact with the aspiration seal portion 92 and the second support portion 93. That is, beginning at the distal end of the outer tube 30, the frictional resistance or frictional coefficient of the outer surface of the outer tube 30 varies from low frictional coefficient (at the distal portion), high frictional coefficient (at an intermediate portion), and low frictional coefficient (at the proximal portion). Therefore, the outer tube 30 can be supported so that a rotational torque of the gripping operation unit 70 is transmitted to the distal side of the medical device 10, or the outer tube 30 itself easily applies the rotational torque to the distal side of the medical device 10. Specifically, a twist or a curve is eliminated in an extracorporeally exposed portion of the outer tube 30. In this manner, the rotational torque of the operation unit 70 can be reliably transmitted to a distal end of the medical device 10.

The distal portion of the outer tube 30 is preferably more flexible than the proximal portion so that the outer tube 30 is bent inside the biological lumen. In order to have flexibility in the distal portion of the outer tube 30, for example, a spiral slit or groove may be formed through laser processing or the like. The processed outer surface of the distal portion of the outer tube 30 may be coated with a resin or the like.

The distal end of the outer tube 30 has an aspiration opening portion 33 for aspirating the cut object or the liquid discharged from the drive shaft 20. The distal end of the outer tube 30 is located on the proximal side of the cutting portion 40. The distal portion of the outer tube 30 has a curved portion 34. The curved portion 34 can be used to change a position and an orientation of the distal end of the outer tube 30 and the cutting portion 40 by rotating the outer tube 30. The proximal end of the outer tube 30 has a proximal opening portion 35 which is open inside a first space portion 95 (to be described later).

The material from which the outer tube 30 may be made preferably has a certain degree of strength. For example, it is possible to preferably use stainless steel, Ta, Ti, Pt, Au, W, or shape memory alloy. The material from which the outer tube 30 may be fabricated may be ABS resin, or engineering plastic resin such as polycarbonate (PC), polymethyl methacrylate (PMMA), polyacetal (POM), polyphenylsulfone (PPSU), polyethylene (PE), carbon fiber, and polyetheretherketone (PEEK).

The cutting portion 40 is a member for cutting an object such as a thrombus. The cutting portion 40 is fixed to the outer peripheral surface of the distal portion of the first drive shaft 22. The outer surface of the cutting portion 40 has many fine abrasive grains. Alternatively, the cutting portion 40 may include a sharp blade.

The material from which the cutting portion 40 may be made preferably has strength which enables the thrombus to be cut. For example, it is possible to preferably use stainless steel, Ta, Ti, Pt, Au, W, shape memory alloy, or super steel alloy.

The inner tube 50 is a flexible tubular body that surrounds the drive shaft 20 inside the outer tube 30. The inner tube 50 surrounds the drive shaft 20 that allows the fluid to pass between the inner surface of the drive shaft 20 and the outer surface of the drive shaft 20, thereby preventing shortcutting of the fluid from the liquid delivering lumen 21 to the aspiration lumen 31 after passing through the drive shaft 20. The inner tube 50 includes a proximal side inner tube 51 and a distal side inner tube 52. The proximal portion of the proximal side inner tube 51 is fixed to the hub unit 60. The distal portion of the proximal side inner tube 51 is located on the proximal side of the central passage portion 27 of the drive shaft 20. The proximal side inner tube 51 effectively transmits the aspiration pressure and the liquid delivering pressure of the hub unit 60 to the central passage portion 27. The distal side inner tube 52 is freely rotatable on the distal side from the interlock portion 25 without being constrained by other members. The distal side inner tube 52 effectively transmits the aspiration pressure and the liquid delivering pressure of the hub unit 60 which are transmitted to the central passage portion 27 further to the distal side. It is desirable that the material from which the inner tube 50 may be fabricated has a certain degree of flexibility and low friction. It is possible to preferably use fluorine-based polymer such as polyether ether ketone (PEEK) and PTFE/ETFE, polymethyl methacrylate (PMMA), polyethylene (PE), polyether block acid copolymer (PEBAX), or polyimide, and a combination thereof.

The hub unit 60 includes a casing 61, the drive unit 62, a switch 63, a liquid delivering port 64, an aspiration port 65, and an electric cable 66. The hub unit 60 further includes the operation unit 70, an aspiration portion 90, and a liquid delivering portion 100.

The casing 61 accommodates the drive unit 62, the liquid delivering portion 100, and the aspiration portion 90. A bearing-shaped first support portion 67 that supports the operation unit 70 to be rotatable is formed in the distal portion of the casing 61.

For example, the drive unit 62 is a hollow motor. The drive unit 62 is rotated by electric power supplied from the outside via the electric cable 66. The drive tube 24 of the drive shaft 20 penetrates through the drive unit 62. The drive tube 24 is directly connected to the hollow drive rotor 62A of the hollow motor without using a bearing or the like. Therefore, the drive unit 62 can rotate the drive shaft 20 around high accurate rotation axis at high speed without deviation. An outer diameter of the drive tube 24 is smaller than an outer diameter of the drive rotor 62A. Therefore, an inner diameter of a second seal portion 103 (to be described later) is reduced when the second seal portion 103 is brought into contact with the outer peripheral surface of the drive tube 24, compared to when the second seal portion 103 is spaced from the outer peripheral surface of the drive tube 24. Therefore, the frictional resistance between the drive tube 24 and the second seal portion 103 is reduced, and sealing performance can be improved. A rotation speed of the drive unit 62 is not particularly limited. For example, the rotation speed is 5,000 to 200,000 rpm. In addition, another tubular body may be disposed between the hollow drive rotor 62A of the hollow motor and the drive shaft 20 in order to improve manufacturing assembly efficiency and electrical safety. The tubular body can be formed of an insulating material such as metal, non-conductive metal, or a resin. Since the hollow motor is used for the drive unit 62, the rotation axes of the drive unit 62 and the drive shaft 20 and the rotation axis of the outer tube 30 can all be coaxial with each other. In this manner, the drive shaft 20 can be very accurately and stably rotated. Moreover, it is possible to solve problems of heat generation and noise caused by drive transmission components such as gears. Furthermore, the hub unit 60 is downsized. Accordingly, an operator can operate the hub unit 60 with one hand. The drive tube 24 may be fixed to the proximal end of the second drive shaft 23 instead of covering the proximal portion of the second drive shaft 23. In addition, the drive tube 24 may not be provided. In this case, the second drive shaft 23 in which the wire rod is spirally wound is sealed by a first seal portion (first seal) 102 and the second seal portion (second seal) 103. A spiral gap of the second drive shaft 23 is covered with solder, an adhesive, or coating, for example. Therefore, a portion of the second drive shaft 23 which comes into contact with the first seal portion 102 and the second seal portion 103 is a tubular body that does not allow circulation between the inner peripheral surface of the first and second seal portions 102, 103 and the outer peripheral surface of the second drive shaft 23.

The electric cable 66 can be connected to an external power source or a control device. The switch 63 is a portion by which an operator operates the driving and stopping of the drive unit 62. The switch 63 is located on the outer surface of the distal portion of the casing 61. Therefore, the operator can operate the operation unit 70, a rotation restriction unit 80, and the switch 63 which are located in the distal portion of the casing 61 with one hand.

The operation unit 70 is operated by the operator with a finger to apply a rotational torque to the outer tube 30. The operation unit 70 is fixed to the outer peripheral surface of the proximal portion of the outer tube 30. The operation unit 70 includes an operation dial 71 and a receiving groove 72. The operation dial 71 is a substantially disk-shaped portion operated by the operator with the finger. The outer peripheral surface of the operation dial 71 has high frictional resistance or frictional coefficient so that the operation dial 71 can be easily operated. The receiving groove 72 is held to be rotatable by the first support portion 67. The frictional coefficient of the receiving groove 72 with respect to the first support portion 67 is high so that an orientation of the outer tube 30 can be held. Therefore, when the finger is released after the operation dial 71 is rotated by the operator, the rotated position is held by the frictional resistance or frictional coefficient between the receiving groove 72 and the first support portion 67. The frictional coefficient between the outer peripheral surface of the outer tube 30 and the inner peripheral surface of the aspiration seal portion 92, the frictional coefficient between the outer peripheral surface of the outer tube 30 and the inner peripheral surface of the second support portion 93, or the frictional coefficient between the outer peripheral surface of the operation unit 70 and the inner peripheral surface of the first support portion 67 is high so that the orientation of the outer tube 30 is held. In this manner, it is possible to obtain the same advantageous effect. In this manner, the number of components can be reduced, and the structure can be simplified.

The liquid delivering port 64 can be connected to a liquid delivering source 11 such as an external liquid delivering pump. A liquid such as a physiological salt solution to be delivered into the living body is supplied from the liquid delivering source 11 to the liquid delivering port 64. The liquid delivering port 64 transports the supplied liquid to the liquid delivering portion 100. The liquid delivering source 11 may have any configuration as long as the liquid delivering pressure can be generated, and it is possible to use a pump, a bag suspended in a drip tower, or a syringe. The liquid delivering source 11 capable of actively delivering the liquid, such as the pump, is used. Accordingly, the liquid delivering amount can be stabilized.

The aspiration port 65 can be connected to an aspiration source 12 such as an external aspiration pump. The aspiration port 65 transports the fluid aspirated by the aspiration source 12 and contained inside the aspiration portion 90, toward the aspiration source 12. The aspiration source 12 may have any configuration as long as the aspiration pressure can be generated, and it is possible to use a pump or a syringe, for example. The aspiration source 12 capable of actively aspirating the fluid, such as the pump, is used. Accordingly, the aspiration pressure can be increased, and the aspiration force can be stabilized and improved.

The aspiration portion 90 applies the aspiration pressure to the aspiration lumen 31 of the outer tube 30. The aspiration portion 90 includes a first housing 91, the aspiration seal portion 92, and the second support portion 93.

The first housing 91 includes an aspiration port 94 that discharges the fluid to the outside, and the first space portion 95 that communicates with the aspiration port 94. The proximal opening portion 35 of the outer tube 30 is located inside the first space portion 95. The proximal side inner tube 51 is fixed to the proximal portion of the first space portion 95. The aspiration port 94 is connected to the aspiration port 65.

The aspiration seal portion 92 is located between the first housing 91 and the outer tube 30 in the distal portion of the first space portion 95. The aspiration seal portion 92 prevents external air from flowing into the first space portion 95. Furthermore, the aspiration seal portion 92 supports the outer tube 30 to be rotatable. That is, the aspiration seal 92 supports the outer tube 30 so that the outer tube 30 is able to rotate. The aspiration seal portion 92 has high dimensional accuracy, a smooth surface shape, and high flexibility (elastic). In this manner, the aspiration seal portion 92 comes into close contact with a contact target with high dimensional accuracy without any gap, and is excellent in sealing performance. Examples of the material from which the aspiration seal portion 92 may be fabricated or made include elastic bodies or elastic materials such as natural rubber, synthetic rubber, and silicone resin. The aspiration seal portion 92 may be disposed in the proximal portion of the first space portion 95. In this manner, the outer tube 30 can be very accurately supported to be rotatable, instead of increasing an entire length of the hub unit 60.

The second support portion 93 is a distal portion of the first space portion 95, and is located between the first housing 91 and the outer tube 30. The second support portion 93 is located on the proximal side of the aspiration seal portion 92. The second support portion 93 preferably has low frictional resistance or frictional coefficient. For example, the material from which the second support portion 93 may be made includes a fluorine-based resin such as ultrahigh molecular weight polyethylene, polyester, polyamide, and polytetrafluoroethylene, ABS resin, polyacetal (POM), polycarbonate (PC), or a combination of two or more materials described above (e.g., polymer alloy, polymer blend, and laminate).

The liquid delivering portion 100 is located on the proximal side of the aspiration portion 90, and is located on the distal side of the drive unit 62. The liquid delivering portion 100 delivers the liquid to the liquid delivering lumen 21 of the drive shaft 20. The liquid delivering portion 100 includes a second housing 101, the first seal portion 102, the second seal portion 103, and a fixing member 106.

The second housing 101 includes a liquid delivering port 104 through which the liquid is delivered from the outside, and the second space portion 105 that communicates with the liquid delivering port 104. The drive shaft 20 penetrates through the inside of the second space portion 105. The proximal passage portion 28 through which the liquid is delivered to the liquid delivering lumen 21 is located inside the second space portion 105. The liquid delivering port 104 is connected to the liquid delivering port 64.

The first seal portion 102 and the second seal portion 103 are located between the second housing 101 and the drive tube 24 of the drive shaft 20 in the proximal portion of the second space portion 105. The first seal portion 102 and the second seal portion 103 prevent the liquid pressurized inside the second space portion 105 from flowing outward. The first seal portion 102 is located on the distal side from the second seal portion 103. Therefore, the first seal portion 102 is closer to an internal space of the second space portion 105 than the second seal portion 103. Therefore, the first seal portion 102 is located on a higher pressure side than the second seal portion 103.

The first seal portion 102 has the inner diameter slightly larger than the outer diameter of the drive tube 24. The first seal portion 102 is separated from the drive tube 24 with a small diameter clearance so that the first seal portion 102 does not come into contact with the drive tube 24 (i.e., the first seal portion 102 does not contact the outer surface of the drive tube 24 along the entire circumferential extent of the first seal portion 102). The first seal portion 102 has a first frictional resistance or frictional coefficient with respect to the rotating drive tube 24. In a case where the first seal portion 102 comes into contact with the drive tube 24, the first frictional coefficient is the frictional resistance or frictional coefficient generated by the contact. In a case where the first seal portion 102 does not come into contact with the drive tube 24, for example, the first frictional resistance or frictional coefficient is the resistance generated by the fluid located between the first seal portion 102 and the drive tube 24. When the drive tube 24 is rotated, the first seal portion 102 and the drive tube 24 may come into contact with each other to some extent. The first seal portion 102 causes a pressure loss in the fluid flowing through a minute flow path between the first seal portion 102 and the drive tube 24. As a result, the fluid pressure in the second seal portion 103 is lower than the fluid pressure in the first seal portion 102. In this manner, the sealing performance required for the second seal portion 103 is reduced. The first seal portion 102 is formed to be long (elongated) in an axial direction so that the pressure loss can be generated as much as possible. Therefore, an axial length of the first seal portion 102 is preferably longer than an axial length of the second seal portion 103. However, a configuration is not limited to this relationship.

A diameter clearance (diameter difference) between the first seal portion 102 and the drive tube 24 is preferably 0.001 to 0.2 mm, more preferably 0.005 to 0.05 mm, and much more preferably 0.005 to 0.02 mm. The material from which the first seal portion 102 may be made preferably has low frictional resistance or frictional coefficient, high heat resistance, a low linear expansion coefficient, and high wear resistance. For example, the material for fabricating the first seal portion 102 includes a fluorine-based resin such as ultrahigh molecular weight polyethylene, polyester, polyamide, polyether ether ketone, and polytetrafluoroethylene, polyacetal (POM), or a combination of two or more materials described above (e.g., polymer alloy, polymer blend, laminate, and coating). The first seal portion 102 may be a portion of the second housing.

The second seal portion 103 is located between the second housing 101 and the drive tube 24 on the proximal side from the first seal portion 102. The second seal portion 103 prevents the liquid passing through the minute flow path between the first seal portion 102 and the drive tube 24 from flowing outward. The second seal portion 103 is formed of a flexible material having higher sealing performance than that of the first seal portion 102. For example, the material which may be used to fabricate the second seal portion 103 includes elastic bodies (elastic materials) such as natural rubber, synthetic rubber, and silicone resin. Since the drive tube 24 rotates at a high speed, the second seal portion 103 spaces from the drive tube 24 not to stick the drive tube 24. When used in combination with the first seal portion 102, the second seal portion 103 can come into weak contact with the drive tube 24. That is, the first seal portion 102 is disposed on the distal side (high pressure side) from the second seal portion 103. Accordingly, the pressing pressure of the second seal portion 103 against the drive tube 24 can be reduced. The second seal portion 103 has a second frictional resistance or frictional coefficient with respect to the rotating drive tube 24. The second frictional coefficient is higher than the first frictional coefficient. In other words, the frictional coefficient of the second seal portion 103 with respect to the rotating drive tube 24 is greater than the frictional coefficient of the first seal portion 102 with respect to the rotating drive tube 24. In a case where the second seal portion 103 comes into contact with the drive tube 24, the second frictional resistance or frictional coefficient is the frictional resistance caused by the contact. In a case where the second seal portion 103 does not come into contact with the drive tube 24, for example, the second frictional resistance or frictional coefficient is the resistance generated by the fluid located between the second seal portion 103 and the drive tube 24. When the contact between the second seal portion 103 and the drive tube 24 is microscopically observed, both of these are in a partial contact state instead of an entire contact state. The first seal portion 102 which has poor sealing performance but has little frictional resistance by virtue of being separated from the drive tube 24 is disposed on the high pressure side of the second seal portion 103. In this manner, the first seal portion 102 and the second seal portion 103 are combined with each other. Accordingly, the frictional resistance or frictional coefficient can be reduced while the sealing performance can be sufficiently achieved. A material of the above-described elastic bodies has high adhesion, but tends to have high friction due to material characteristics. As a method of solving the disadvantage, a low friction material whose inner diameter is very accurately processed can be used. In this manner, the friction can be further reduced while the adhesion is maintained. Even in this case, the frictional resistance or frictional coefficient can be reduced by reducing a contact area with the drive tube 24.

The fixing member 106 is a tubular member that fixes the second seal portion 103 to the second housing 101. The fixing member 106 prevents the second seal portion 103 from being detached or being shifted. The fixing member 106 enters the inside of the second space portion 105 from the proximal side of the second housing 101. The distal end of the fixing member 106 comes into contact with the proximal side surface of the second seal portion 103, and supports the second seal portion 103. The fixing member 106 is fixed to the second housing 101 by adhesion or screwing.

Next, a method of using the medical device 10 according to the present embodiment will be described. This method of use will be described by way of example in a case of destroying and aspirating a lesion area such as a thrombus inside a blood vessel.

Figure 4A:
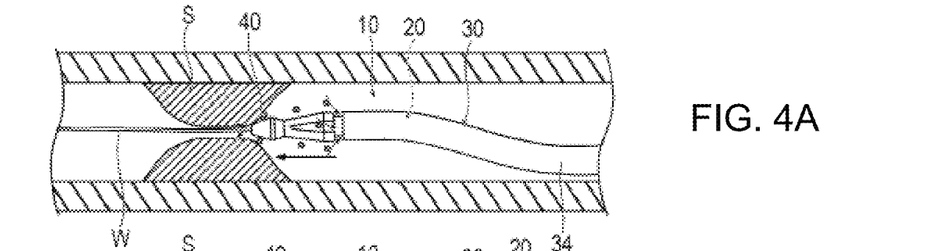
FIG. 4A illustrates a state where the medical device starts cutting.

First, an operator inserts a guide wire W into the blood vessel so that the guide wire W reaches the vicinity of a lesion area S. Next, the operator inserts a proximal end of the guide wire W into the liquid delivering lumen 21 of the medical device 10. Thereafter, as illustrated in FIG. 4A, the cutting portion 40 of the medical device 10 is moved to the vicinity of the lesion area S while being guided by the guide wire W.

Next, the operator operates the switch 63 to start liquid delivering and aspirating. That is, the operator operates the external liquid delivering source 11 and the aspiration source 12. Simultaneously or after a lapse of a prescribed time, the cutting portion 40 is rotated via the drive shaft 20. The operation can be controlled by a device connected to the electric cable 66, or can be controlled by disposing a control unit inside the hub unit 60. In this manner, the operator can cut the lesion area S.

Figure 4B:
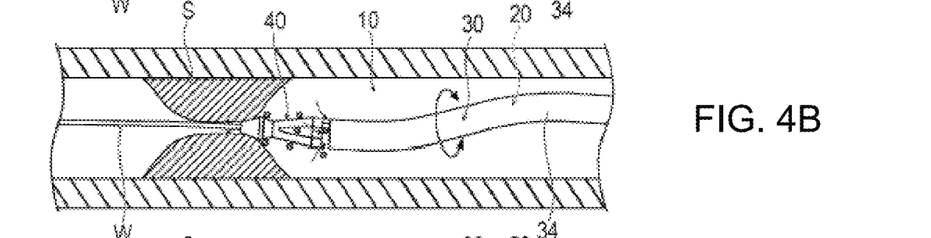
FIG. 4B illustrates a state where the medical device performs the cutting while rotating an outer tube.
Figure 4C:
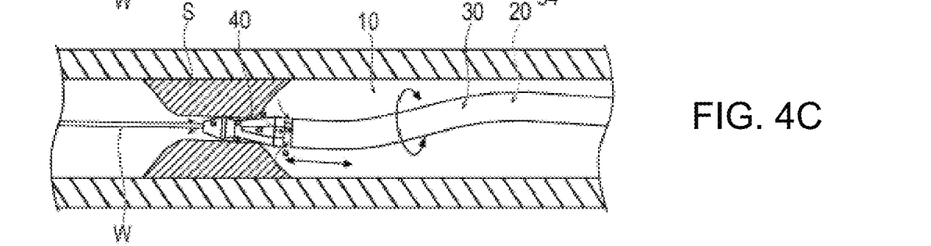
FIG. 4C illustrates a state where the medical device performs the cutting while moving the outer tube.

As illustrated in FIG. 2, the operator can operate the operation unit 70 in a case where the operator wants to change a position of the cutting portion 40 in a circumferential direction. When the operator rotates the operation dial 71, the operation unit 70 supported by the first support portion 67 is rotated. In this manner, the outer tube 30 is rotated. When the outer tube 30 is rotated, a direction of the curved portion 34 of the outer tube 30 is changed. As illustrated in FIG. 4B, the position of the cutting portion 40 can be changed. Therefore, the cutting can be performed while the direction of the cutting portion 40 is changed without rotating the whole hub unit 60 which is less likely to be largely rotated. Furthermore, the operator moves the whole hub unit 60 or the extracorporeally exposed outer tube 30, and causes the outer tube 30 to reciprocate along a longitudinal direction of the blood vessel. In this manner, as illustrated in FIG. 4C, the lesion area S can be cut along the longitudinal direction of the blood vessel by the cutting portion 40.

When the liquid delivering starts, as illustrated in FIG. 2, the physiological salt solution (saline solution) flowing into the second space portion 105 from the liquid delivering port 104 passes through the proximal passage portion 28 of the drive shaft 20, and enters the liquid delivering lumen 21. The drive shaft 20 and the second housing 101 are sealed by the first seal portion 102 and the second seal portion 103. Therefore, the physiological salt solution in the second space portion 105 is unlikely to flow out from between the drive shaft 20 and the second housing 101. Therefore, the second space portion 105 can maintain the high liquid delivering pressure. In addition, the first seal portion 102 which has poor sealing performance but has little frictional resistance or frictional coefficient is disposed on the high pressure side of the second seal portion 103. In this manner, the first seal portion 102 and the second seal portion 103 are combined with each other (operate in combination with one another). Accordingly, the frictional resistance or frictional coefficient can be reduced while the sealing performance can be sufficiently achieved. Therefore, the drive shaft 20 can be rotated with high transmission efficiency.

The physiological salt solution entering the liquid delivering lumen 21 moves to the distal side or in the distal direction. The proximal side inner tube 51 is located outside the drive shaft 20. Therefore, the physiological salt solution inside the liquid delivering lumen 21 can effectively move to the central passage portion 27 without shortcutting to the aspiration lumen 31. When a portion of the physiological salt solution inside the liquid delivering lumen 21 reaches the central passage portion 27, the physiological salt solution moves to the aspiration lumen 31.

The rest of the physiological salt solution inside the liquid delivering lumen 21 further moves to the distal side or in the distal direction, and is discharged into the blood vessel from the discharge opening portion 29 through the inside of the cutting portion 40 as illustrated in FIG. 3. A portion of the physiological salt solution entering the inside of the blood vessel is aspirated into the aspiration lumen 31 of the outer tube 30 together with the blood and the cut object(s). The object(s) and the fluid which enter the aspiration lumen 31 move to the proximal side or in the proximal direction through the aspiration lumen 31. As illustrated in FIG. 2, the fluid entering the aspiration lumen 31 is diluted by the physiological salt solution that merges in the central passage portion 27. Therefore, the thrombus can be prevented from being formed inside the aspiration lumen 31, and an aspiration amount can be increased by lowering viscosity of the aspirated object. Therefore, the aspiration performance can be improved while a decreases in the aspiration force of the medical device 10 or damage to the medical device 10 is prevented. In addition, the thrombus formed inside the medical device 10 can be prevented from flowing out into the biological lumen. When the fluid entering the aspiration lumen 31 reaches the first space portion 95 of the aspiration portion 90, the fluid is discharged from the aspiration port 94 to the external aspiration source 12. The first housing 91 of the aspiration portion 90 and the outer tube 30 are sealed by the aspiration seal portion 92. Therefore, it is possible to prevent a decrease in the aspiration pressure of the first space portion 95. The aspiration pressure at this time is 0 to 90 kPa, preferably 0 kPa to 50 kPa when absolute vacuum is set to 0 kPa.

After the cutting and aspiration of the lesion area S are completed, the operator presses the switch 63. As a result, the rotation of the drive shaft 20 is stopped and the cutting by the cutting portion 40 is stopped. Simultaneously or after a lapse of a prescribed time, the liquid delivering and the aspirating are stopped. That is, the external liquid delivering source 11 and the aspiration source 12 are stopped. The operation can be controlled by a device connected to the electric cable 66, or can be controlled by disposing a control unit inside the hub unit 60. Thereafter, the medical device 10 is removed from the blood vessel, and the treatment is completed.

As described above, according to the present embodiment, there is provided the medical device 10 for removing the object inside the biological lumen. The medical device 10 includes the rotatable drive shaft 20, the outer tube 30 that accommodates the drive shaft 20 to be rotatable, the cutting portion 40 fixed to the distal portion of the drive shaft 20 to cut the object, and the hub unit 60 disposed in the proximal portion of the drive shaft 20 and the outer tube 30. The hub unit 60 has the first housing 91 having the aspiration port 94 for discharging the fluid to the outside, and causing the aspiration lumen 31 of the outer tube 30 to communicate with the aspiration port 94, the second housing 101 having the liquid delivering port 104 for delivering the liquid from the outside, and causing the liquid delivering lumen 21 of the drive shaft 20 to communicate with the liquid delivering port 104, the first seal portion 102 disposed between the second housing 101 and the drive shaft 20, and having the first frictional resistance or frictional coefficient, and the second seal portion 103 disposed between the second housing 101 and the drive shaft 20, and having the second frictional resistance or frictional coefficient. The first frictional coefficient is lower than the second frictional coefficient, and the first seal portion 102 is located on a distal side of the second seal portion 103.

According to the medical device 10 configured as described above, the first seal portion 102 having the relatively lower frictional coefficient is disposed on the high pressure side of the second seal portion 103 having the relatively higher frictional coefficient. In this manner, the first seal portion 102 and the second seal portion 103 are combined with each other (work in combination with one another). Accordingly, the frictional resistance or frictional coefficient can be reduced while the sealing performance can be sufficiently achieved. Therefore, the medical device 10 can effectively transmit the rotational torque to the cutting portion 40 by using the relatively lower frictional coefficient while obtaining the high aspiration pressure by using the relatively higher sealing performance.

In addition, the clearance between the first seal portion 102 and the drive shaft 20 is larger than the clearance between the second seal portion 103 and the drive shaft 20. In this manner, according to the medical device 10, the first seal portion 102 which has relatively poorer sealing performance but has little frictional resistance or frictional coefficient so as to be separated from the drive shaft 20 is disposed on the high pressure side of the second seal portion 103. In this manner, the first seal portion 102 and the second seal portion 103 are combined with each other. Accordingly, the frictional resistance or frictional coefficient can be reduced while the sealing performance can be sufficiently achieved. Therefore, the medical device 10 can effectively transmit the rotational torque to the cutting portion 40 by using the relatively lower frictional coefficient while obtaining the high aspiration pressure by using the relatively high sealing performance. In addition, during the high speed rotation, the drive shaft 20 has an axial deviation to some extent, and a rotation orbit drawn by the drive shaft 20 increases toward the distal side in the circumferential direction. In order to cope with the deviation, the present embodiment adopts the structure in which the clearance increases toward the distal side or in the distal direction. Accordingly, it is possible to reduce the rotational torque loss caused by unnecessary friction.

In addition, the second seal portion 103 comes into contact with (contacts) the drive shaft 20. Therefore, the second seal portion 103 achieves the relatively high sealing performance. Therefore, according to the medical device 10, the first seal portion 102 having the relatively low frictional resistance and the second seal portion 103 having the relatively high sealing performance are combined with each other. Accordingly, the frictional resistance or frictional coefficient can be reduced while the sealing performance is sufficiently achieved.

In addition, the first seal portion 102 and the second seal portion 103 are formed of different materials. In this manner, the medical device 10 can individually provide characteristics suitable for each of the first seal portion 102 and the second seal portion 103.

In addition, the first seal portion 102 has the frictional coefficient smaller than that of the second seal portion 103.

In this manner, the medical device 10 can maintain high sealing performance obtained by the flexible second seal portion 103.

In addition, the second seal portion 103 is more flexible than the first seal portion 102. In this manner, according to the medical device 10, the torque transmission efficiency can be improved by the first seal portion 102 having the small frictional resistance.

The portion of the drive shaft 20 which comes into contact with the first seal portion 102 and the second seal portion 103 is the tubular body (for example, the drive tube 24) that does not allow circulation between the inner peripheral surface of the drive tube 24 and the outer peripheral surface of the drive shaft 20. Therefore, the first seal portion 102 and the second seal portion 103 can achieve the sealing performance with the drive shaft 20.

In addition, the hub unit 60 has the drive unit 62 that is directly connected to the proximal side from the second seal portion 103 of the drive shaft 20 and rotates the drive shaft 20. For example, the drive unit 62 has the hollow drive rotor 62A, and the drive rotor 62A is connected to the drive tube 24 of the drive shaft 20. The drive tube 24 and the drive rotor 62A may be integrally formed. However, in order to obtain rigidity that can withstand high speed rotation, it is necessary to provide the drive rotor 62A having a prescribed outer diameter (2 to 10 mm, and preferably 2 to 3 mm). On the other hand, in order to improve the sealing performance, the frictional resistance or frictional coefficient is minimized by reducing a diameter of a sealing target portion. The drive tube 24 having the outer diameter smaller than that of the drive rotor 62A (for example, 0.5 to 9 mm for the drive tube 24, and preferably 0.7 mm to 1.5 mm for the drive rotor 62A) is disposed as a separate body from the drive rotor 62A. In this manner, the high speed rotation and the low friction of the drive shaft 20 can be compatibly achieved. In this manner, the drive shaft 20 can be directly rotated by the drive unit 62 without using drive transmission component such as gears. Therefore, even if the drive shaft 20 is rotated at the high speed, the drive shaft 20 is rotated around the high accurate rotation axis, and the deviation is less likely to occur. As a result, even if the drive shaft 20 is rotated at the high speed, the clearance between the first seal portion 102 and the second seal portion 103 is maintained at a proper value that can obtain a desired advantageous effect. Therefore, according to the medical device 10, the rotational torque can be effectively transmitted to the cutting portion 40 while the high aspiration pressure is maintained. In addition, according to this configuration, the rotation axes of the drive unit 62 and the drive shaft 20 and the rotation axis of the outer tube 30 can all be coaxial with each other. In this manner, the drive shaft 20 can be very accurately and stably rotated. Moreover, it is possible to solve problems of heat generation and noise caused by drive transmission components such as gears. Furthermore, the hub unit 60 is downsized. Accordingly, an operator can operate the hub unit 60 with one hand.

The present invention is not limited to the above-described embodiments, and various modifications can be made by those skilled in the art within the technical idea of the present invention. For example, the biological lumen into which the medical device 10 is inserted is not limited to the blood vessel, and may be a vessel, a ureter, a bile duct, a fallopian tube, or a hepatic duct, for example. Therefore, the object to be destroyed may not be the thrombus.

In addition, both the first seal portion 102 and the second seal portion 103 may come into contact with the drive shaft 20. Therefore, the first frictional resistance and the second frictional resistance are frictional resistances generated by the contact therebetween. For example, the first seal portion 102 comes into contact with the drive shaft 20 with a relatively weak contact force, and the second seal portion 103 comes into contact with the drive shaft 20 with a relatively strong contact force. Even in this case, according to the medical device 10, the first seal portion 102 having the low frictional resistance or frictional coefficient and the second seal portion 103 having the high sealing performance are combined with each other. Accordingly, the frictional resistance can be reduced while the sealing performance can be sufficiently achieved.

Figure 5A:
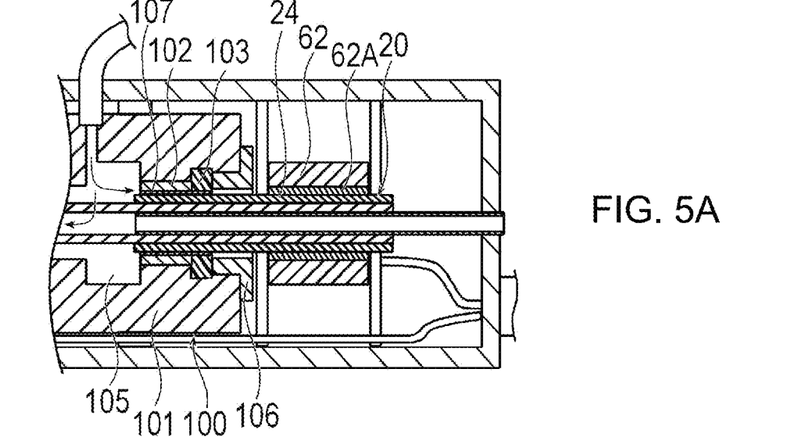
FIG. 5A illustrates a first modification example.

In addition, according to a first modification example illustrated in FIG. 5A, the first seal portion 102 and the second seal portion 103 may be coated with a high viscosity material 107. The high viscosity material 107 preferably has biocompatibility, and includes silicone oil or olive oil, for example. The high viscosity material 107 has higher viscosity than water, for example. In this manner, the sealing performance between the first seal portion 102 and the drive tube 24 is improved, and the liquid is less likely to move between the second seal portion 103 and the drive tube 24, thereby improving the sealing performance. In this manner, the medical device 10 can have improved aspiration efficiency. Alternatively, at least one of the first seal portion 102 and the second seal portion 103 may be coated with a hydrophobic material. In this manner, water is repelled from the first seal portion 102 and the second seal portion 103, and the sealing performance of the first seal portion 102 and the second seal portion 103 is improved. Furthermore, at least one of the first seal portion 102 and the second seal portion 103 may be coated with a hydrophilic material. In this manner, the sealing performance may be improved by covering the surface with moisture to prevent air from entering.

Figure 5B:
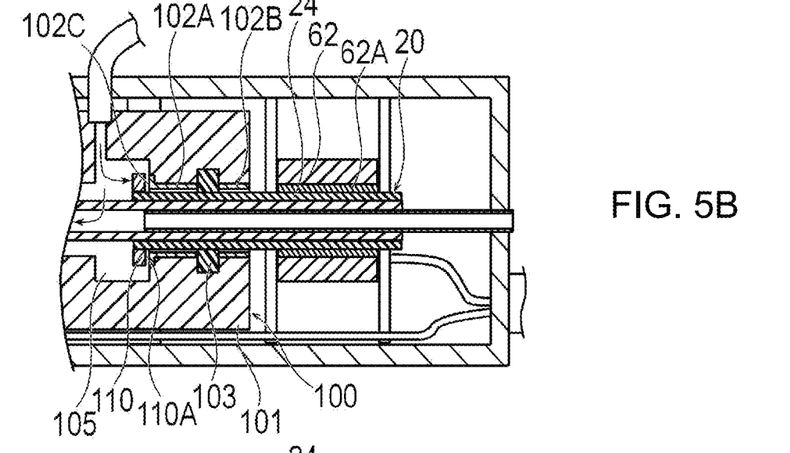
FIG. 5B illustrates a second modification example.

In addition, as in a second modification example illustrated in FIG. 5B, the first seal portion may have a first seal portion (first seal) 102B on the proximal side in addition to a first seal portion 102A on the distal side of the second seal portion 103. The first seal portion 102B on the proximal side is separated from the drive tube 24. The first seal portion 102B can also cause the pressure loss by forming a minute flow path between the first seal portion 102B and the drive tube 24. In addition, the drive shaft 20 may have a ring-shaped seal assisting portion 110 that protrudes in the radial direction inside the second space portion 105. A proximal surface 110A of the seal assisting portion 110 is close to a distal surface 102C of the first seal portion 102A. Between the proximal surface 110A and the distal surface 102C, minute flow paths that cause pressure loss are formed. In this manner, according to the medical device 10, a long minute flow path between the first seal portion 102A and the drive shaft 20 can be formed without lengthening the first seal portion 102A in the axial direction. Therefore, the medical device 10 can achieve the high sealing performance while suppressing instability of rotation due to the lengthening of the drive shaft 20.

Figure 5C:
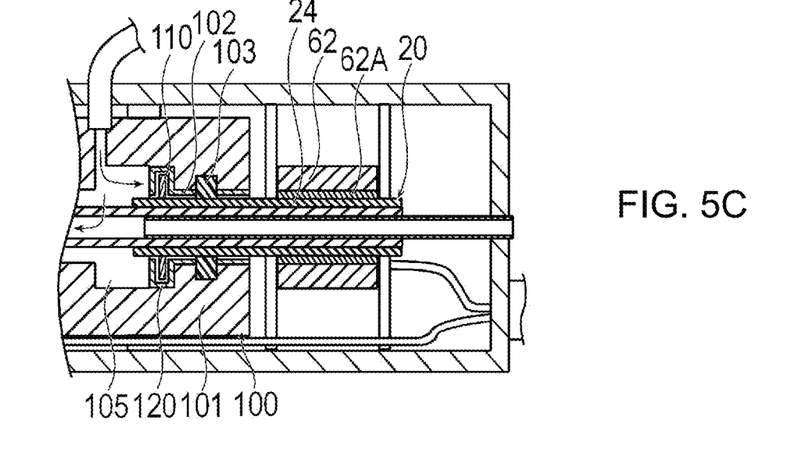
FIG. 5C illustrates a third modification example.

In addition, as in a third modification example illustrated in FIG. 5C, the seal assisting portion 110 of the drive shaft 20 may be located inside a wall surface of the second housing 101 on the proximal side from the second space portion 105. An accommodating portion 120 that can accommodate the seal assisting portion 110 is formed inside the wall surface of the second housing 101. The wall surface of the accommodating portion 120 is a portion of the first seal portion 102. Therefore, the first seal portion 102 is adjacent to all of the distal surface, the proximal surface, and the outer peripheral surface of the seal assisting portion 110. In this manner, according to the medical device 10, a long minute flow path between the first seal portion 102 and the drive shaft 20 can be formed without lengthening the first seal portion 102 in the axial direction. Therefore, the medical device 10 can achieve the high sealing performance while suppressing instability of rotation due to the lengthening of the drive shaft 20.

Figure 6A:
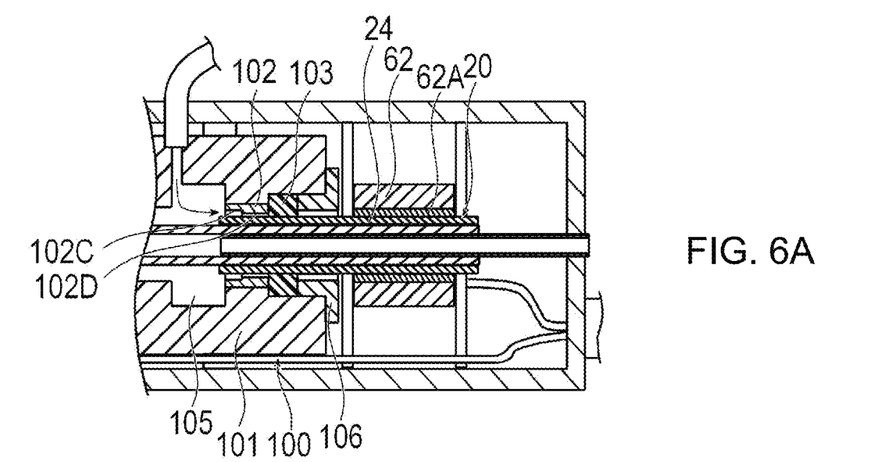
FIG. 6A illustrates a fourth modification example.

In addition, as in a fourth modification example illustrated in FIG. 6A, the first seal portion 102 may include the large diameter portion 102C having a larger inner diameter and a smaller diameter portion 102D having a smaller inner diameter. The large diameter portion 102C is located on the distal side of the small diameter portion 102D. Since the first seal portion 102 has the large diameter portion 102C, the first seal portion 102 is less likely to come into contact with the drive shaft 20 even when the axis of the drive shaft 20 deviates due to the rotation. Therefore, the medical device 10 is less likely to be damaged. In this modification example, a plurality of the large diameter portions 102C having the larger inner diameter and a plurality of the small diameter portions 102D having the smaller inner diameter are provided in a stepped shape, but may be provided in a tapered shape from the distal portion to the proximal portion.

Figure 6B:
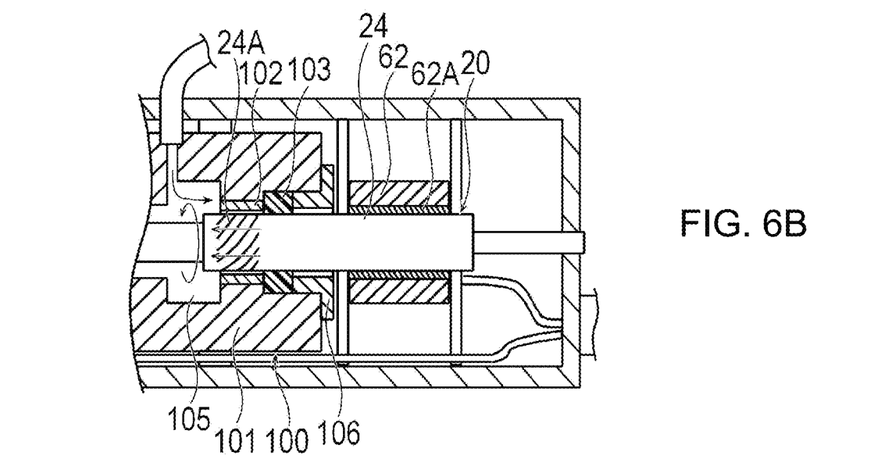
FIG. 6B illustrates a fifth modification example.

In addition, as in a fifth modification example illustrated in FIG. 6B, a convex or concave spiral portion 24A may be formed on the outer peripheral surface of the drive tube 24 located inside the first seal portion 102. The spiral portion 24A functions as an axial flow type impeller, and pushes the fluid back to the distal side or in the distal direction. In this manner, the fluid flowing toward the proximal side or proximal direction can be pushed back toward the distal side by rotating the drive shaft 20. When an effect of moving the fluid to the distal side by the spiral portion 24A is too high, the air is drawn into the second space portion 105. Therefore, it is preferable that the spiral portion 24A has an effect of generating a flow which is equal to or weaker than a flow to the proximal side.

In addition, the first housing 91 and the second housing 101 may be integrally formed.

In addition, the aspiration port 94 of the aspiration portion 90 may be open to the atmospheric pressure without being connected to the aspiration source 12. Even according to this configuration, in a case where the pressure inside the biological lumen is higher than the atmospheric pressure, the aspiration portion 90 can aspirate the object inside the biological lumen.

The detailed description above describes embodiments of a medical device and method representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object inside a biological lumen, the medical device comprising:
   a rotatable drive shaft that includes a lumen;
   an outer tube that accommodates the drive shaft so that the drive shaft is rotatable, the outer tube including a lumen in which flows fluid during operation of the medical device;
   a cutting portion fixed to a distal portion of the drive shaft to cut the object;
   a hub unit disposed in a proximal portion of the drive shaft and the outer tube;
   the hub unit comprising:
      a first housing that includes an aspiration port for discharging the fluid to outside the medical device, the lumen of the outer tube being in fluid communication with the aspiration port so that at least some of the fluid in the lumen of the outer tube flows into the aspiration port during operation of the medical device;
      a second housing that includes a liquid delivering port for delivering a liquid from outside the medical device, the lumen of the drive shaft being in communication with the liquid delivering port;
      a first seal portion disposed between the second housing and the drive shaft, the rotatable drive shaft being rotatable relative to the first seal portion, the first seal portion having a first frictional with respect to the rotatable drive shaft during rotation of the rotatable drive shaft;
      a second seal portion disposed between the second housing and the drive shaft, the rotatable drive shaft being rotatable relative to the second seal portion, the second seal portion having a second frictional coefficient with respect to the rotatable drive shaft during rotation of the rotatable drive shaft; and
      the first frictional coefficient being lower than the second frictional coefficient, and the first seal portion being located on a distal side of the second seal portion.

2. The medical device according to claim 1, wherein a clearance exists between an inner surface of the first seal portion and an outer surface of the drive shaft, and a clearance exists between an inner surface of the second seal portion and the outer surface of the drive shaft, the clearance between the inner surface of the first seal portion and the outer surface of the drive shaft is larger than the clearance between the inner surface of the second seal portion and the outer surface of the drive shaft.

3. The medical device according to claim 1, wherein the second seal portion comes into contact with the drive shaft during operation of the medical device.

4. The medical device according to claim 1, wherein the first seal portion and the second seal portion come into contact with the drive shaft during operation of the medical device.

5. The medical device according to claim 1, wherein the first seal portion and the second seal portion are formed of different materials.

6. The medical device according to claim 1, wherein the second seal portion is more flexible than the first seal portion.

7. The medical device according to claim 1, wherein a portion of the drive shaft comes into contact with the first seal portion and the second seal portion during operation of the medical device, the portion of the drive shaft which comes into contact with the first seal portion and the second seal portion during operation of the medical device is a tubular body having no circulation between an inner peripheral surface tubular body and an outer peripheral surface tubular body.

8. The medical device according to claim 1, wherein the drive shaft includes a ring-shaped seal assisting portion that protrudes in a radial direction, and the first seal portion is adjacent to at least one of a distal surface of the seal assisting portion, a proximal surface of the seal assisting portion, and an outer peripheral surface of the seal assisting portion.

9. The medical device according to claim 1, wherein the hub unit includes a drive unit directly connected to the drive shaft at a position proximal of the second seal portion to rotatably drive the drive shaft.

10. The medical device according to claim 1, wherein at least one of the first seal portion and the second seal portion is coated with a high viscosity material.

11. A medical device for removing an object inside a biological lumen, the medical device comprising:
an outer tube that includes a lumen, the lumen including an open distal end that opens to outside the outer tube at a distal end portion of the outer tube;
a rotatable drive shaft having an outer surface and accommodated in the lumen of the outer tube so that the drive shaft accommodated in the lumen of the outer tube is rotatable relative to the outer tube, the drive shaft including a lumen possessing an open distal end that opens to outside the drive shaft at a distal end portion of the drive shaft, and including a space between an outer surface of the drive shaft and an inner surface of the outer tube;
a cutter fixed to the distal end portion of the drive shaft and rotatable together with the rotatable drive shaft to cut the object;
a housing in which is located a space, the housing including a liquid delivering port that communicates with the space in the housing so the liquid flowing through the liquid delivering port flows into the space in the housing, the lumen of the drive shaft being in communication with the space in the housing so that liquid entering the space in the housing by way of the liquid delivering port enters the lumen in the drive shaft and at least some of the liquid entering the lumen in the drive shaft flows along the lumen in the drive shaft and flows out through the open distal end of the lumen in the drive shaft;
the drive shaft passing through the space in the housing;
a first seal surrounding the drive shaft and possessing an inner surface and an outer surface, the first seal being positioned between the housing and the drive shaft so that the outer surface of the first seal faces the housing and the inner surface of the first seal faces the outer surface of the drive shaft, the rotatable drive shaft being rotatable relative to the inner surface of the first seal, the inner surface of the first seal having a first frictional coefficient with respect to the outer surface of the rotatable drive shaft during rotation of the rotatable drive shaft;
a second seal surrounding the drive shaft and possessing an inner surface and an outer surface, the second seal being positioned between the housing and the drive shaft so that the outer surface of the second seal faces the housing and the inner surface of the second seal faces the outer surface of the drive shaft, the rotatable drive shaft being rotatable relative to the second seal portion, the inner surface of the second seal having a second frictional coefficient with respect to the outer surface of the rotatable drive shaft during rotation of the rotatable drive shaft;
the second seal being positioned proximal of the first seal; and
the first frictional coefficient being different from the second frictional coefficient.

12. The medical device according to claim 11, wherein the first frictional coefficient is less than the second frictional coefficient.

13. The medical device according to claim 11, wherein the housing is one housing, and further comprising an other housing, the other housing including an interior space, the other housing including an aspiration port that communicates with the interior space in the other housing so that a fluid in the interior space in the other housing is discharged to outside the medical device by way of the aspiration port, the interior space in the other housing being in fluid communication with the space between the outer surface of the drive shaft and the inner surface of the outer tube.

14. The medical device according to claim 13, wherein the other housing is positioned distal of the one housing.

15. The medical device according to claim 13, further comprising an inner tube that surrounds a portion of the drive shaft, the inner tube being surrounded by the outer tube with a space between an inner surface of the outer tube and an outer surface of the inner tube, the drive shaft includes a part passing through the interior space in the other housing, the inner tube surrounding an entirety of the part of the drive shaft passing through the interior space in the other housing.

16. The medical device according to claim 15, wherein the inner tube and the outer tube both possess a proximal-most end, the proximal-most end of the inner tube being positioned proximal of the proximal-most end of the outer tube.

17. The medical device according to claim 13, further comprising a tubular fixing member that fixes a position of the second seal, the tubular fixing member being separate from the one housing, being positioned proximal of the second seal and being in direct contact with the second seal.

18. The medical device according to claim 11, wherein the housing is one housing, and further comprising an other housing having an interior space, one portion of the drive shaft being positioned in the interior space in the one housing and another portion of the drive shaft being positioned in the interior spaced in the other housing, the other housing including an aspiration port that communicates with the interior space in the other housing so that a fluid in the interior space in the other housing is discharged to outside the medical device by way of the aspiration port, the first housing and the second housing being located in a casing.

19. A method comprising:
inserting a cutter into a biological lumen and advancing the cutter in the biological lumen to position the cutter adjacent an object in the lumen that is to be removed, the cutter being connected to a distal portion of a rotatable drive shaft so that the cutter rotates together with the drive shaft, the drive shaft including a lumen and being accommodated in a lumen in an outer tube so that the outer tube surrounds the drive shaft, the lumen in the drive shaft communicating with a space in a housing, the drive shaft passing through the housing with a portion of the drive shaft located in the housing, the drive shaft having an outer surface;
rotatably driving the drive shaft to rotate the cutter while the cutter is in contact with the object to cut the object;
introducing liquid into the space in the housing so that the liquid enters the lumen in the drive shaft and at least some of the liquid in the lumen in the drive shaft flows in a distal direction and flows out of the lumen in the drive shaft by way of an open end of the lumen, the open end of the lumen in the drive shaft being at the distal portion of the drive shaft;
sealing the drive shaft and the housing by way of two seals positioned proximal of the space in the housing to prevent the liquid introduced into the space of the housing from flowing out between the drive shaft and the second housing, the two seals including a first seal having an inner surface facing the outer surface of the drive shaft and a second seal having an inner surface facing the outer surface of the drive shaft;

the first and second seals being positioned between the housing and the drive shaft with the first seal on a distal side of the second seal, the first seal; and the rotatably driving of the drive shaft causing the outer surface of the drive shaft to rotate relative to both the inner surface of the first seal and the inner surface of the second seal, the first seal having a first frictional coefficient with respect to the outer surface of the drive shaft during the rotatable driving of the drive shaft, the second seal having a second frictional coefficient with respect to the outer surface of the drive shaft during the rotatable driving of the drive shaft the second frictional coefficient being different from the first frictional coefficient.

20. The method according to claim 19, wherein the housing is one housing, and further comprising aspirating fluid from the biological lumen so that the fluid enters and flows along the lumen in the outer tube and is introduced into a space in an other housing, the fluid in the space in the other housing being aspirated out of the space by way of an aspiration port in the other housing, the other housing being located distal of the one housing.

* * * * *